United States Patent [19]
Tanaka

[11] Patent Number: 5,820,824
[45] Date of Patent: Oct. 13, 1998

[54] APPARATUS FOR MIXING AND SUCKING A LIQUID SAMPLE

[75] Inventor: Yosuke Tanaka, Kobe, Japan

[73] Assignee: Toa Medical Electronics Co., Ltd., Kobe, Japan

[21] Appl. No.: 768,464

[22] Filed: Dec. 18, 1996

[30] Foreign Application Priority Data

Dec. 19, 1995 [JP] Japan ................................. 7-350708
Dec. 19, 1995 [JP] Japan ................................. 7-350709

[51] Int. Cl.$^6$ ................................................. B01L 3/02
[52] U.S. Cl. ...................... 422/100; 422/101; 436/180; 73/864.17; 73/863.32
[58] Field of Search .......................... 422/58, 59, 60, 422/61, 99, 100, 101, 102, 103, 104; 436/180; 73/864.17, 863.32

[56] References Cited

U.S. PATENT DOCUMENTS

| | | | |
|---|---|---|---|
| 4,000,973 | 1/1977 | Petersen | 436/180 |
| 4,323,537 | 4/1982 | Mody | 422/63 |
| 4,451,433 | 5/1984 | Yamashita et al. | 422/63 |
| 4,528,158 | 7/1985 | Gilles et al. | 422/63 |
| 4,568,520 | 2/1986 | Ackermann et al. | 422/66 |
| 4,730,631 | 3/1988 | Schwartz | 134/155 |
| 4,734,261 | 3/1988 | Koizumi et al. | 422/100 |
| 4,820,497 | 4/1989 | Howell | 422/63 |
| 5,080,868 | 1/1992 | Elgas | 422/99 |
| 5,254,311 | 10/1993 | Ushikubo | 422/81 |
| 5,660,796 | 8/1997 | Sheehy | 422/100 |

*Primary Examiner*—Harold Y. Pyon
*Attorney, Agent, or Firm*—Greenblum & Bernstein, P.L.C.

[57] ABSTRACT

An apparatus for efficiently mixing and sucking a sample capable of performing sucking collection from a sample plural times even when the amount of the sample contained in a vessel is small and requiring a shortened processing time, is provided comprising a first pipet having a through-hole for mixing a liquid sample contained in a vessel by sucking the liquid sample from the vessel through the through-hole and discharging the liquid sample thus sucked into the vessel; and a second pipet having a through-hole having an inner diameter different from that of the through-hole of the first pipet for collecting the sample from the vessel through the through-hole thereof by suction, the first and second pipets being integral with each other.

13 Claims, 4 Drawing Sheets

FIG. 5(a) ASCENT/DESCENT OF THE FIRST AND SECOND PIPETS

FIG. 5(b) SUCTION-DISCHARGE BY THE FIRST PIPET INTERNAL WASHING OF THE FIRST PIPET

FIG. 5(c) SUCTION BY THE SECOND PIPET INTERNAL WASHING OF THE SECOND PIPET

FIG. 5(d) EXTERNAL WASHING OF THE FIRST AND SECOND PIPETS

APPARATUS FOR MIXING AND SUCKING A LIQUID SAMPLE

BACKGROUND OF THE INVENTION

1. Field of the Invention

The present invention relates to apparatus for mixing and sucking a liquid sample and, more particularly, to apparatus for mixing a liquid sample contained in a vessel in, for example, an automatic analyzing system to homogenize the liquid sample and sucking the sample thus homogenized to subject it to predetermined analyses.

2. Description of the Prior Art

Conventionally known apparatus for mixing and sucking a liquid sample such as urine or blood are of the type adapted to perform a suction-discharge mixing process in which an operation of sucking a predetermined amount of a sample contained in a vessel and then jettingly discharging the sucked sample back into the vessel is repeated several times in order to homogenize the distribution state of material components of the sample, and thereafter to collect a predetermined amount of the sample from the vessel by sucking.

Such apparatus includes a vertically disposed single pipet adapted to perform the suction-discharge mixing of the sample contained in the vessel, for example, a test tube.

To homogenize the distribution state of material components of a sample by the suction-discharge mixing process using such apparatus, it is required that the amount of the sample to be sucked and discharged by the pipet be larger than that to be collected by suction after the mixing. In addition, the suction-discharge process is required to be completed in a relatively short time. For these reasons the pipet is designed to have an inner diameter equal to or larger than prescribed.

When a sample is collected by suction using such pipet thus designed, the sample is sucked in an amount substantially the same as the amount needed for the mixing. This often raises a problem that the sucking collection of a sample plural times becomes impossible when the amount of the sample in the vessel is small, though such problem does not occur where the amount of the sample in the vessel is sufficiently large.

Further, since the suction-discharge mixing and the sucking collection of the sample are achieved by the single pipet, the pipet cannot be subjected to washing until the sucking collection and its following operations are completely finished. This causes difficulties in shortening the processing time and in making the process efficient.

It is therefore an object of the present invention to provide an apparatus for mixing and sucking a liquid sample which is capable of performing sucking collection of the sample plural times even when the amount of the sample contained in a vessel is small and offers an efficient processing taking a shortened time.

SUMMARY OF THE INVENTION

According to the present invention, there is provided an apparatus for mixing and sucking a liquid sample, comprising: a first pipet having a through-hole (inner passage) for mixing the liquid sample contained in a vessel by sucking the liquid sample from the vessel through the through-hole and discharging the liquid sample thus sucked into the vessel; and a second pipet having a through-hole having an inner diameter different from that of the through-hole of the first pipet for collecting the sample from the vessel through the through-hole thereof by suction, the first and second pipets being integral with each other.

In the present invention the vessel containing the liquid sample to be mixed and sucked is appropriately selected from various vessels of different sizes and shapes made of different materials. One example thereof is a so-called tapered test tube containable about 5 to about 10 ml of a sample such as urine or blood.

The first pipet serves to suck a predetermined amount of the sample contained in the vessel and discharge the sample thus sucked back into the vessel jettingly. By this operation the sample contained in the vessel is sucked into the first pipet and then jetted against the bottom of the vessel so as to be extended along the bottom wall or side wall of the vessel. Such operation is repeated several times to complete the suction-discharge mixing process through the first pipet. The suction-discharge operation of the first pipet is achieved by utilizing the suction-discharge function of, for example, a diaphragm pump adapted for suction and discharge.

After the completion of the suction-discharge mixing process by the first pipet, the second pipet sucks the sample from the vessel for collection. Usually a fixed amount of the sample is collected using a sample quantity determining means such as a sampling valve. The sucking operation of the second pipet is achieved by utilizing the sucking function of, for example, a syringe-type sucking pump.

The first and second pipets are those formed of stainless steel or a plastic and have through-holes of different inner diameters. Typically, the through-hole of the first pipet for suction-discharge mixing is larger in inner diameter than that of the second pipet for sucking collection. This is because in general the amount of a sample required for suction-discharge mixing is larger than that required for sucking collection.

The first and second pipets may be unified into a single tube pipet by bonding, jointing or fusion-bonding, or may be formed into an integral one having two tube portions by, for example, molding. Preferably, the first and second pipets each have an outer diameter as small as possible so as to be inserted into a thin vessel such as a thin test tube.

The foregoing and other objects, features and attendant advantages of the present invention will be readily apparent from the following detailed description of the preferred embodiments of the invention in conjunction with the accompanying drawings.

DETAILED DESCRIPTION OF THE PREFERRED EMBODIMENTS

The apparatus for mixing and sucking a sample according to the present invention is usually equipped with a pipet raising/lowering means for raising and lowering the pipets, a washing means for washing the interior and exterior of the pipets and desired flow paths, a waste liquid chamber for containing a waste liquid, a control unit for controlling the suction-discharge mixing of the sample, the sucking collection of the sample and the washing of the pipets, and like components, in addition to the first and second pipets, the sample quantity determining means, the pump for suction-discharge and the pump for suction.

Preferably, the mixing and sucking apparatus of the present invention is so constructed that: the first pipet is connected at a top end thereof to a first pump for suction and discharge through a main chamber and a subchamber; the second pipet is connected to a second pump for suction through a sampling valve; the main chamber serves to mix the sample sucked into the first pipet by the first pump; the subchamber serves to prevent the sample from flowing into the first pump; and the sampling valve serves to determine the quantity of the sample to be sucked into the second pipet by the second pump.

The sample sucked by the first pipet flows into the main chamber where the sample is extended so as to be mixed sufficiently because the main chamber usually has an inner diameter larger than that of the first pipet.

The subchamber is disposed, for example, in the vicinity of the main chamber, specifically above or laterally of the main chamber and is connected at, for example, its upper portion to an upper portion or a like portion of the main chamber through an upper connecting portion or the like. The subchamber is connected at, for example, its upper portion to the first pump for providing the first pipet with a suction-discharge driving power. Stated otherwise, the subchamber is disposed between the main chamber and the first pump. The suction-discharge operation of the first pump may cause the sample to flow into the subchamber from the main chamber. In this case, the subchamber serves to prevent the sample from flowing into the first pump.

The upper connecting portion may comprise a connecting tube (either rigid or flexible) or a connecting tube portion which are separate from or integral with the main chamber and the subchamber. The inner diameter of the upper connecting portion is not particularly limited but is preferably smaller than that of the upper portion of the main chamber or the upper portion of the subchamber, and more preferably smaller than that of the upper portion of any of the main chamber and the subchamber.

The mixing and sucking apparatus of the present invention preferably further includes a washing fluid supply line connected to the main chamber for supplying a washing fluid to the main chamber, and a washing spit for washing the first and second pipets.

The washing fluid supply line is connected to an upper portion or a like portion of the main chamber and supplies the washing fluid to the main chamber after the mixing of the sample is completed. The term "washing fluid" herein used means a liquid or air for washing. The washing fluid supplied from the supply line to the main chamber mostly flows down into the pipets but partly flows into the subchamber.

The mixing and sucking apparatus of the present invention preferably further includes a first waste liquid line connected to the washing spit for collecting a waste washing liquid from the first and second pipets.

The first waste liquid line serves to collect the waste washing liquid resulting from the washing of the exterior and interior of the pipets by guiding it into a waste liquid chamber or the like. The first waste liquid line is usually disposed between the washing spit and the waste liquid chamber.

More preferably, the mixing and sucking apparatus of the present invention further includes a first waste liquid line connected to the washing spit for collecting a waste washing liquid from the first and second pipets, and a second waste liquid line connected to the subchamber for collecting a waste washing liquid from the subchamber.

The second waste liquid line serves to collect the sample and/or the washing fluid that flow into the subchamber by guiding the same into the waste liquid chamber or the like.

The main chamber and subchamber are not particularly limited with regard to their shapes, specifically the shapes of their internal spaces. However, each chamber preferably has an upper internal wall shaped substantially circular or substantially elliptic in horizontal section.

Where the upper internal wall of the main chamber is shaped substantially circular or substantially elliptic in horizontal section, the washing fluid supply line is preferably connected to the upper internal wall of the main chamber substantially horizontally tangential thereto. If this is the case, the washing fluid supplied from the washing fluid supply line is introduced into the main chamber along the upper internal wall thereof and helically flows down while washing the internal wall of the main chamber, and then enters the pipets and flows down while washing the internal surfaces thereof. With this feature, it is possible to efficiently and reliably wash the internal surfaces of the main chamber and pipets without a need of supplying an excessive amount of the washing fluid to the main chamber.

The control unit is preferably capable of issuing an instruction to cause the second pipet to collect the sample by suction immediately after the completion of the mixing of the sample by the first pipet. The expression "immediately after" herein used is meant to include the meaning of "simultaneously with" or "in a very short time after" comparable to the "simultaneously with". Such a control unit enables the advantages of the invention brought by the provision of the first and second pipets to be enhanced efficiently.

Further, the control unit is preferably capable of issuing an instruction to provide a timing lag between the washing of the first pipet and that of the second pipet. If the washing of each pipet can be performed independently, it becomes possible to perform an air blow operation against the washing liquid remaining within one pipet (for example, the first pipet) during the washing of the other pipet (for example, the second pipet).

The present invention will be more fully described by reference to an embodiment shown in the drawings.

Figure 1:
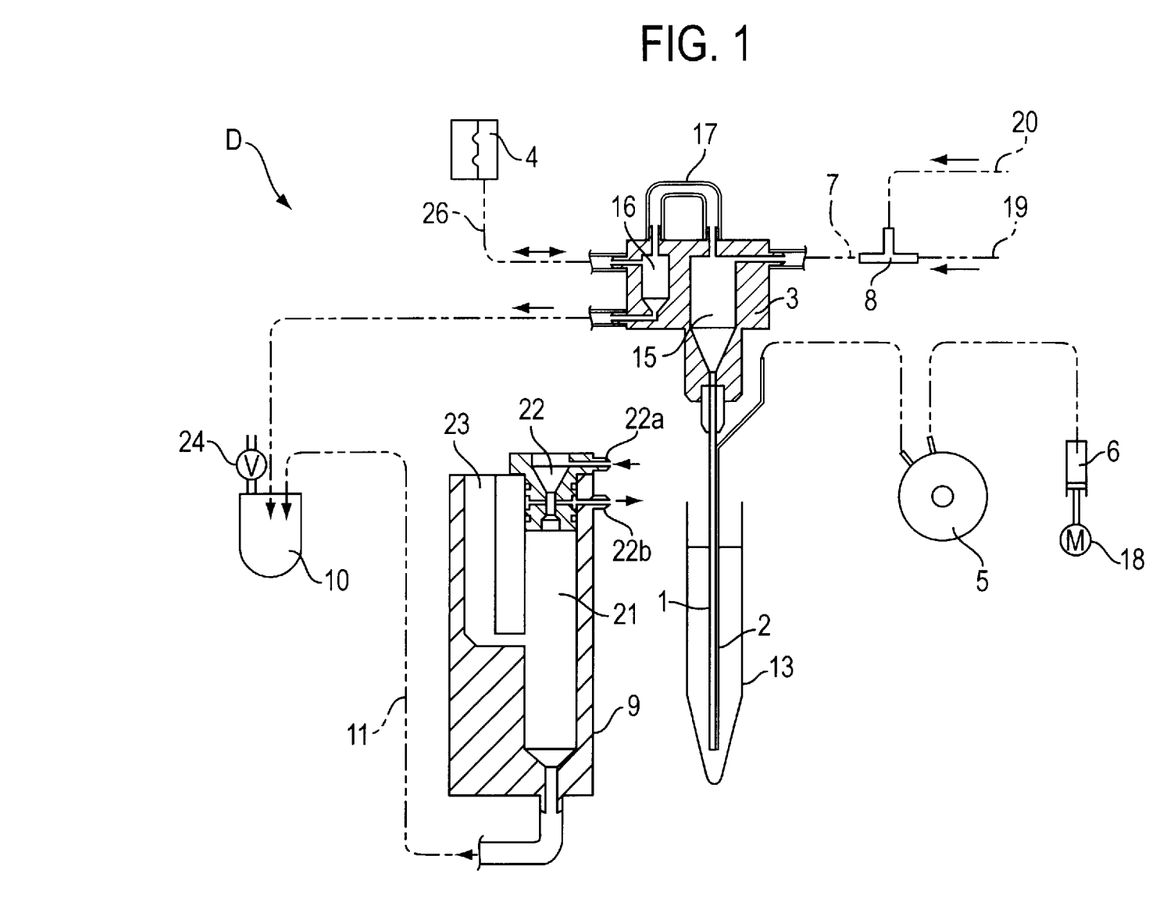
FIG. 1 is a schematic view of the overall configuration of an apparatus for mixing and sucking an sample according to one embodiment of the present invention.

FIG. 1 schematically illustrates the overall configuration of apparatus D for mixing and sucking a sample according to one embodiment of the present invention. The apparatus D shown includes a first pipet 1, a second pipet 2, a mixing chamber 3, a diaphragm pump 4 serving as a first pump for suction and discharge, a sampling valve 5, a syringe-type pump 6 serving as a second pump for suction, a washing fluid supply line 7, a washing spit 9, a waste liquid chamber 10, a first waste liquid line 11, a second waste liquid line 12, and a control unit (not shown). Reference numeral 13 denotes a tapered test tube serving as a vessel for containing a sample. The test tube 13 contains about 4.0 ml up to 10 ml (maximum) of a crude urine (liquid sample).

Figure 2:
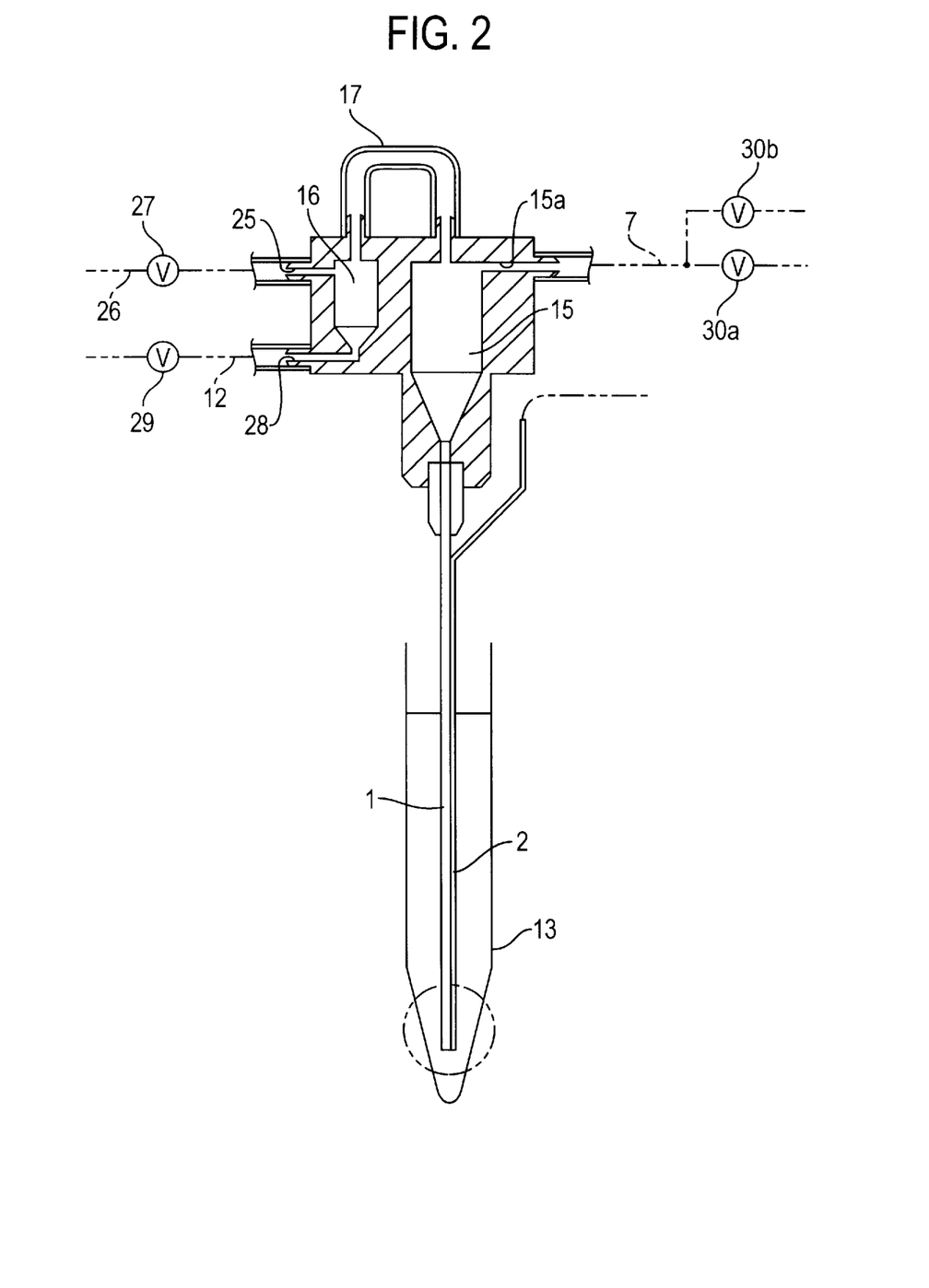
FIG. 2 is an enlarged schematic view showing an principal part of the apparatus shown in FIG. 1.
Figure 3:
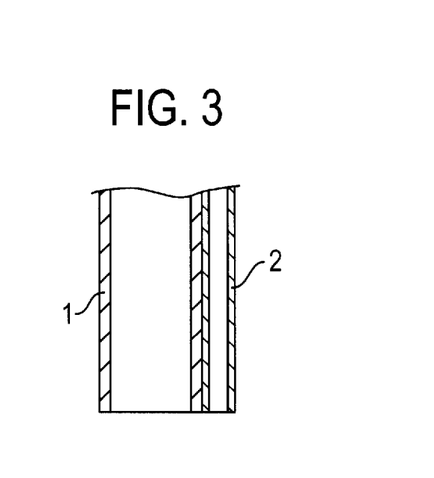
FIG. 3 is an enlarged longitudinal sectional view showing lower end portions of first and second pipets of the apparatus shown in FIG. 1.
Figure 4A:
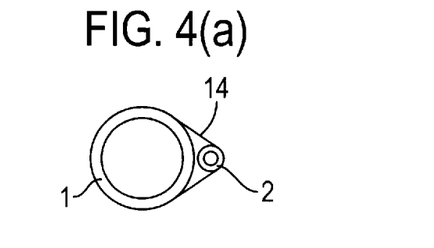
FIGS. 4a and 4b are an enlarged bottom view showing the lower end portions of the first and second pipets shown in FIG. 3.
Figure 4B:
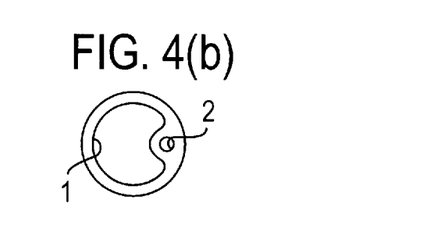
Figure 5A:
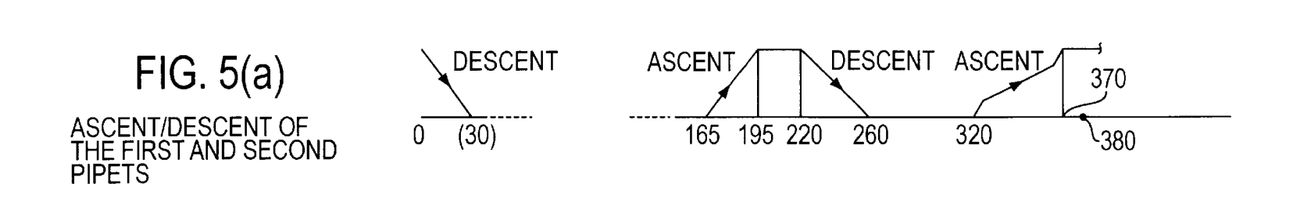
FIGS. 5a, 5b, 5c and 5d are a timing chart for explaining various operations of the apparatus shown in FIG. 1.
Figure 5B:
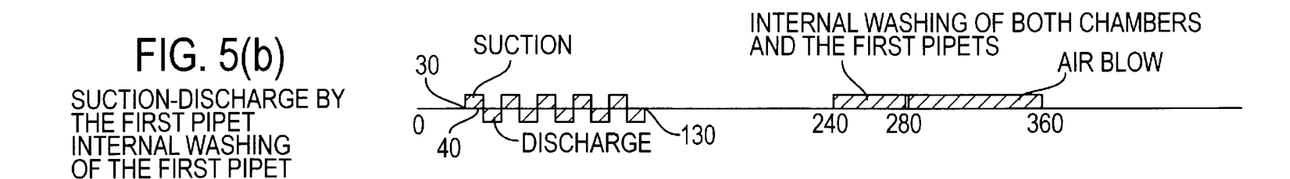
Figure 5C:
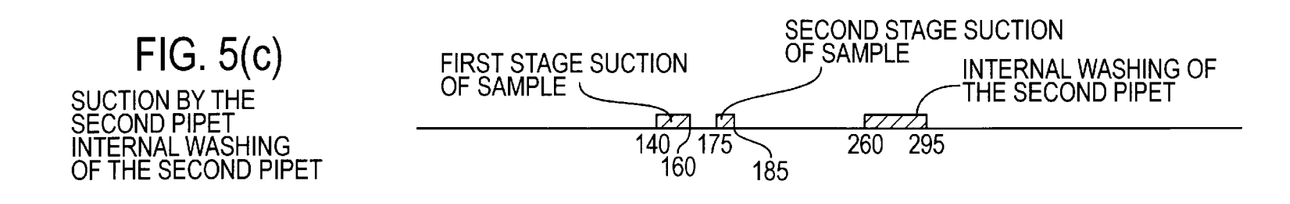
Figure 5D:
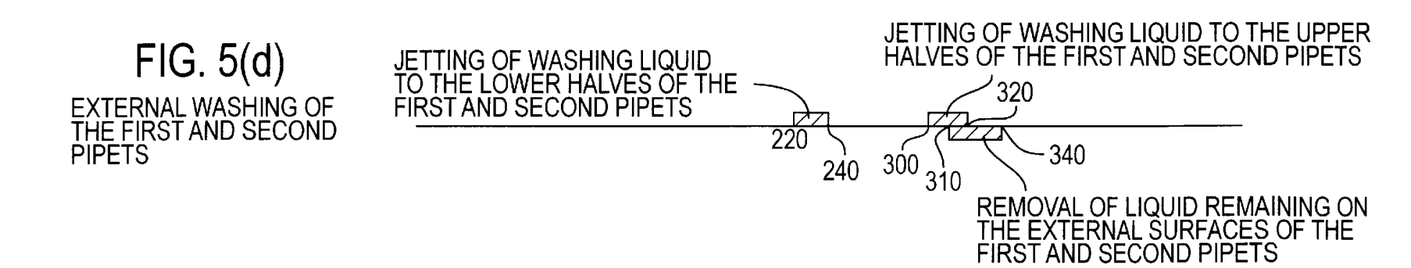

The first pipet 1 comprises a stainless steel cylinder having a through-hole of a uniform inner diameter and serves to perform suction-discharge mixing of the crude urine contained in the test tube 13. The second pipet 2 comprises a stainless steel cylinder having a through-hole of a uniform inner diameter and serves to perform suction collecting of the sample from the test tube 13 after the first pipet 1 completes the suction-discharge mixing of the sample. As shown in enlarged views in FIGS. 2 and 3, the through-hole of the first pipet 1 has a relatively large inner diameter (2.0 mm), while that of the second pipet 2 has a relatively small inner diameter (0.7 mm). As shown in enlarged view in FIG. 4(*a*), the two pipets 1 and 2 are integrally joined together in a parallel fashion by bonding their external walls to each other with a thermoplastic resin adhesive. Reference numeral 14 in FIG. 4(*a*) denotes a joint portion of the two pipets 1 and 2. Instead of the pipets 1, 2 shown in FIG. 4(*a*), it is possible to employ pipets 1 and 2 integrally plastic-molded into a single cylinder having a larger through-hole and a smaller through-hole as shown in FIG. 4(*b*).

The mixing chamber 3 comprises a main chamber 15 connected to and disposed above the first pipet 1 and a subchamber 16 disposed laterally of the main chamber 15.

The main chamber 15 has an upper internal wall defining an internal space shaped circular in horizontal section and a lower internal wall tapered gradually thinner as having a lower end portion connected to an upper end of the first pipet. Since the main chamber 15 has such an internal space, the crude urine sucked up by the first pipet 1 flows into the main chamber 15 where the urine is extended and hence mixed sufficiently.

The subchamber 16 has an internal space shaped similar to that of the main chamber 15. The subchamber 16 is located so that the top end of its internal space is positioned at the same level as that of the main chamber 15. The capacity of the subchamber 16 is about one-fifth of that of the main chamber 15.

The upper end portion of the main chamber 15 is connected to the upper end portion of the subchamber 16 for communication therebetween through a U-shaped connecting tube 17 forming an upper connecting portion. The upper end portion of the peripheral wall of the main chamber 15 defines a connecting port 15*a*, the axis of which extends horizontally tangential to the internal wall of the upper end portion of the main chamber 15.

The suction-discharge operation of the pump 4 causes the first pipet 1 to suck and discharge the crude urine. The sampling valve 5 determines the quantity of the crude urine to be collected and collects the determined quantity from the crude urine sucked by the second pipet 2. The sucking operation of the pump 6 driven by a motor 18 causes the second pipet 2 to perform suction.

The washing fluid supply line 7 is connected to the connecting port 15*a* of the main chamber 15 and is provided with a T-shaped branch portion 8 for supplying a mixture of a pressurized washing liquid (0.5 kg/cm$^2$) and pressurized air (0.5 kg/cm$^2$) in a predetermined mixing ratio or either of the two to the main chamber 15. The pressurized washing liquid and the pressurized air are introduced from a first supply line 19 and a second supply line 20, respectively. The first supply line 19 is provided with an open/close valve 30*a* for introducing or shutting off the flow of the washing liquid, while the second supply line 20 is similarly provided with an open/close valve 30*b* for introducing or shutting off the flow of the pressurized air.

The washing spit 9 is used in washing the exterior and interior of the first and second pipets 1 and 2. The washing spit 9 comprises a waste liquid receiving part 21 for receiving a waste liquid resulting from the washing, a washing part 22 located above and contiguous to the waste liquid receiving part 21, and an air discharge part 23 located laterally of the waste liquid receiving part 21 for communication therewith. In an upper portion of the washing part 22 is provided a single washing liquid inlet port 22*a* extending horizontally, the axis of which extends tangential to the washing part 22. A pressurized washing liquid (0.5 kg/m$^2$) same as above is introduced into the washing part 22 through the washing liquid inlet port 22*a*. An air sucking port 22*b* is provided in a lower portion of the internal wall of the washing part 22 as horizontally radially branched into eight. The air sucking port 22*b* is connected to a vacuum pump of 400 mmHg (not shown).

The waste liquid chamber 10 is provided with a valve 24 for opening the inside of the chamber 10 to the atmosphere. The waste liquid chamber 10 is connected to the waste liquid receiving part of the spit 9 through the first waste liquid line 11.

A single connecting port 25 is horizontally provided in an upper end portion of the peripheral wall of the subchamber 16 and is connected to the pump 4 through a suction-discharge mixing line 26 provided with a valve 27 for opening and closing this line 26.

In a lower end portion of the peripheral wall of the subchamber 16 is horizontally provided a single connecting port 28 connected to the waste liquid chamber 10 through the second waste liquid line 12. The second waste liquid line 12 is also provided with a valve 29 for opening and closing this line 12.

Various operations of the mixing and sucking apparatus D will be described with reference to the timing chart shown in FIG. 5. All the operations of the apparatus D are controlled by the aforementioned control unit. Numerical figures on the abscissa axis of the chart represent time from the starting of operation of the apparatus D. For instance, 165 indicates a time point upon lapse of 16.5 seconds from the starting of operation of the apparatus D.

Upon the starting of the apparatus D the first and second pipets 1 and 2 in their home position above and outside the test tube 13 descend at a constant speed so as to be inserted into the test tube 13. Upon lapse of 3.0 seconds the pipets 1,2 stop descending, and the pump 4 is actuated to effect the suction-discharge operation, so that the first pipet 1 performs suction-discharge of the crude urine five times, once every 1.0 second.

More specifically, the control unit causes the valve 27 to be opened, the valve 29 to be closed, the valve 30 to be closed, and the pump 4 to perform a sucking operation. This allows the first pipet 1 to suck up 2.0 ml of the crude urine from the test tube 13 into the main chamber 15, where the sucked urine is extended. At this time, the level of the sucked urine reaches about the half of the depth of the main chamber 15. The sucked urine flowing into the main chamber 15 is sufficiently mixed by being extended within the main chamber 15. A portion of the sucked crude urine which is forcibly introduced into the subchamber 16 (usually in droplets) through the connecting tube 17 by the sucking operation of the first pipet 1 is collected in the bottom portion of the subchamber 16. The crude urine collected to a predetermined amount in the subchamber 16 is guided to the waste liquid chamber 10 by opening the valves 29 and 24.

Once the sucking operation of the pipet 1 is completed, the control unit causes the pump 4 to perform a discharge operation. This allows the first pipet 1 to discharge the crude urine from the main chamber 15 against the bottom of the test tube 13 jettingly. The crude urine thus discharged is extended along the bottom wall or side wall of the test tube 13 so as to be sufficiently mixed in the test tube 13.

Such a suction-discharge operation is repeated five times to complete the suction-discharge mixing by the first pipet 1 (13.0 seconds after the starting of operation of the apparatus D).

Upon lapse of 1.0 second after the completion of the suction-discharge mixing by the first pipet 1, the pump 6 is actuated to perform an sucking operation, so that the second pipet 2 is caused to suck up 0.8 ml of the crude urine from a point adjacent the bottom of the test tube 13 taking 2.0 seconds (first stage suction). 0.5 seconds thereafter, the first and second pipets 1,2 start ascending at a constant speed. 1.0 second after the start of ascending, the second pipet 2 performs a sucking operation again to suck about 0.8 ml of air only (second stage suction), whereby the crude urine sucked by the first stage suction is guided to a deeper portion of the mixing and sucking apparatus D by means of the pressure of the air thus sucked. Even during the second stage suction the first and second pipets 1,2 continue to ascend.

The crude urine thus introduced into the sampling valve 5 by such two-stage suction is subjected to a quantity determination.

Upon lapse of 3.0 seconds after the start of ascending of the first and second pipets 1,2, they stop ascending to resume their home position (19.5 seconds after the starting of operation of the apparatus D). In turn, the first and second pipet 1,2 are moved rearward from the home position so as to be positioned above the washing spit 9 disposed within an analyzing system.

Upon lapse of 22.0 seconds from the starting of operation of the apparatus D, the first and second pipets 1,2 begin descending into the spit 9. Then, the external surfaces of the lower halves of the pipets 1,2 are washed taking 2.0 seconds. Specifically, while the lower halves of the pipets 1,2 descend from the washing part 22 toward the waste liquid receiving part 21, the pressurized washing liquid is jettingly introduced into the washing part 22 through the washing liquid inlet port 22a thereby washing the external surfaces of the lower halves of the pipets 1,2.

During this process the first and second pipets 1,2 continue to descend within the spit 9. Upon completion of the washing of the external surfaces of the lower halves of the first and second pipets 1,2 (24.0 seconds after the starting of operation of the apparatus D), the main chamber 15, subchamber 16 and the interior of the first pipet 1 start being washed.

More specifically, the control unit causes the valves 27 and 29 to be closed, and the valve 30 to be opened so as to supply the mixture of the pressurized washing liquid and pressurized air to the fluid supply line 7 for 2.0 seconds. This allows the mixture to be introduced through the connecting port 15a into the main chamber 15 along the internal wall of the upper end portion of the main chamber 15 (26.0 seconds after the starting of operation of the apparatus D). The mixture thus introduced flows down helically along the internal wall of the main chamber 15 into the first pipet 1, and further flows down while washing the internal surface of the first pipet 1. The descent of the first and second pipets 1,2 is stopped upon lapse of 26.0 seconds after the starting of operation of the apparatus D.

And then, the control unit causes the valve 29 to be opened to supply the mixture to the fluid supply line 7 for 2.0 seconds. This allows most of the mixture to be introduced through the connecting port 15a into the main chamber 15 along the internal wall of the upper end portion of the main chamber 15 and a portion of the mixture to be introduced through the connecting tube 17 into the subchamber 16. The portion of the mixture thus introduced into the main chamber 15 washes the internal wall of the main chamber 15 and the internal surface of the first pipet 1 as described above. The portion of the mixture thus introduced into the subchamber 16 washes the internal wall of the subchamber 16, and is collected within the subchamber 16, then guided to the waste liquid chamber 10.

The waste liquid resulting from the washing of the insides of the main chamber 15 and first pipet 1 is collected in the waste liquid receiving part 21.

When the washing of the insides of the main chamber 15, subchamber 16 and first pipet 1 with the mixture as described above is completed, a residual liquid in droplets remaining in these components is removed taking 8.0 seconds from a time point after lapse of 28.0 seconds from the starting of operation of the apparatus D.

In more detail, pressurized air is supplied to the fluid supply line 7 for 2.0 seconds with the valve 27 closed, the valve 29 opened and the valve 20 opened. Subsequently, pressurized air is supplied to the fluid supply line 7 for 6.0 seconds with the valve 27 closed, the valve 29 closed and the valve 30 opened. These operations cause the residual liquid remaining on the internal walls of the main chamber 15 and subchamber 16 and on the internal surface of the first pipet 1 to be blown away by pressurized air (air blow) and guided to the waste liquid chamber 10 and to the waste liquid receiving part 21 of the spit 9.

The internal surface of the second pipet 2 is washed in the following manner. The control unit actuates a washing mechanism (not shown) to cause the pressurized liquid to be introduced into the second pipet 2, thus washing the internal surface of the second pipet 2 for 3.5 seconds from a time point upon lapse of 26.0 seconds after the starting of operation of the apparatus D.

Upon lapse of 30.0 seconds from the starting of operation of the apparatus D, washing of the outer surfaces of the first and second pipets 1,2 is initiated. At this time the first and second pipets 1,2 are left stationary at their lowermost position within the spit 9. In this condition the lower halves of the first and second pipets 1,2 are situated in the waste liquid receiving part 21 of the spit 9 and lower portions of the upper halves thereof in the washing part 22.

With the first and second pipets 1,2 being in this condition, the pressurized liquid is jettingly introduced into the washing part 22 through the inlet port 22a for 2.0 seconds. This allows the lower portions of the upper halves of the first and second pipets 1,2 to be washed (32.0 seconds after the starting of operation of the apparatus D). Immediately thereafter, the first and second pipets 1,2 ascend, and the ascending speed thereof is lowered to a fixed ascending speed from a predetermined location within the spit 9. The ascending speed of the first and second pipets 1,2 is then increased to a fixed ascending speed from a predetermined location within the spit 9. After 37.0 seconds from the staring of operation of the apparatus D, the first and second pipets 1,2 stop ascending. At this time the first and second pipets 1,2 are positioned above and outside the spit 9.

In parallel with such operations, a liquid in droplets remaining on the external surfaces of the first and second pipets 1,2 is removed. In this operation the control unit actuates the vacuum pump to suck air through the air sucking port 22b of the washing part 22, so that the liquid on the external surfaces of the first and second pipets 1,2 is dropped into the waste liquid receiving part 21.

The mixing and sucking apparatus D is capable of suction-discharge mixing the crude urine contained in the test tube 13 by means of the first pipet 1 having a larger diameter and, independently of the suction-discharge mixing, capable of performing sucking collection by means of the second pipet 2 having a smaller diameter. Thus, even when a small amount of crude urine is contained in the test tube 13, the second pipet 2 adapted for sucking collection enables suction of a smaller amount of the crude urine than is sucked and discharged by the first pipet 1 adapted for suction-discharge mixing. Hence, it is possible eliminate the disadvantage that performing sucking collection from a sample plural times becomes impossible as the case may be.

The mixing and sucking apparatus D is controlled such that immediately after the completion of the suction-discharge mixing process by the first pipet 1, the sucking collection by the second pipet 2 is initiated. Therefore, prior to or during the washing of the first pipet 1 finished with suction-discharge mixing, the second pipet 2 is possible to perform the succeeding sucking collection of crude urine immediately after the suction-discharge mixing process. This makes it possible to shorten the time required for the mixing and sucking operations.

Further, the mixing and sucking apparatus D thus constructed enjoys the following outstanding advantages.

That is, the two pipets 1 and 2 can be inserted into a thin test tube or a like thin vessel at the same time since they are formed integral with each other.

Since the two pipets 1 and 2 are independent of each other, it becomes possible to provide a timing lag between the washing of the first pipet 1 and that of the second pipet 2 thereby shortening the time required for the mixing and sucking process and rendering the overall process of the apparatus D highly efficient.

The first pipet 1 is larger in inner diameter than the second pipet 2. This feature allows the second pipet 2 adapted for sucking collection to suck a smaller amount of a sample than is sucked and discharged by the first pipet 1 adapted for suction-discharge mixing when a desired amount to be suction-discharge mixed of a sample is larger than a desired amount to be suction-collected of the sample and the amount of the sample contained in a vessel is relatively small. Thus, it is possible to eliminate the disadvantage that performing sucking collection from a sample plural times becomes impossible as the case may be.

The mixing and sucking apparatus D is controlled such that immediately after the completion of the suction-discharge mixing by the first pipet 1, the sucking collection by the second pipet 2 is initiated. This makes it possible to further shorten the time required for the mixing and sucking process.

Further, since the apparatus D is controlled to perform the washing of the first pipet 1 and the washing of the second pipet 2 with a timing lag therebetween, it is possible to optimize the timing and the time period for the washing operation following the mixing and sucking process.

While the preferred embodiments of the present invention have been described in detail, it is to be understood that various modifications may be made to the embodiments by those skilled in the art without departing from the spirit and scope of the invention as defined by the following claims.

What is claimed is:

1. An apparatus for mixing and sucking a liquid sample, comprising:

a first pipet having a first wall and a first inner passage, said first inner passage having a first inner diameter;

a first pump, connected to said first pipet, said first pump capable of causing said first pipet to suck a predetermined amount of the liquid sample and to discharge the liquid sample, to thereby mix the liquid sample contained in a vessel by sucking the liquid sample from the vessel through the first inner passage and discharging the liquid sample thus sucked into the vessel; and a second pipet having a second wall and a second inner passage, said second inner passage having a second inner diameter smaller than said first inner diameter;

a second pump connected to said second pipet, said second pump capable of causing said second pipet to suck a quantity of liquid sample through said second inner passage, for collecting the sample from the vessel through the second inner passage by suction;

said first and second pipets being integrally joined together at said first and second walls; and wherein the first and second pipets being unified into a single tube pipet by bonding, jointing, fusion-bonding or molding.

2. An apparatus as set forth in claim 1, wherein said first and second pipets comprise cylinders of stainless steel integrally bonded to each other with a thermoplastic resin adhesive.

3. An apparatus as set forth in claim 1, wherein said first and second pipets are integrally molded of a plastic into a single cylinder having two parallel inner passages as said first and second inner passages.

4. An apparatus as set forth in claim 1 wherein said first and second pipets are integrally joined together in a parallel fashion.

5. An apparatus as set forth in claim 1, further comprising a control unit for controlling said mixing and suction of said liquid sample by said first pipet, said suction of said liquid sample by said second pipet, and washing of said first and second pipets with a washing fluid.

6. An apparatus as set forth in claim 5, wherein said control unit is capable of issuing an instruction to cause said second pipet to collect said quantity of liquid sample by suction immediately after said mixing of said liquid sample by said first pipet is completed.

7. An apparatus as set forth in claim 5, wherein said control unit is capable of issuing an instruction to provide a timing lag between said washing of said first pipet and said washing of said second pipet.

8. An apparatus as set forth in claim 1, further comprising:

said first pipet is connected at a top end thereof to said first pump through a main chamber and a subchamber;

said second pipet is connected to said second pump through a sampling valve;

said main chamber serves to mix said predetermined amount sucked into said first pipet by said first pump;

said subchamber serves to prevent said predetermined amount from flowing into said first pump; and said sampling valve serves to determine said quantity of liquid sample to be sucked into said second pipet by said second pump.

9. An apparatus as set forth in claim 8, further comprising a washing fluid supply line connected to said main chamber for supplying a washing fluid to said main chamber.

10. An apparatus as set forth in claim 9, wherein:

said main chamber has an upper internal wall shaped substantially circular or substantially elliptic in horizontal section; and said washing fluid supply line is connected to said upper internal wall tangentially thereto.

11. An apparatus as set forth in claim 8, further comprising a washing fluid supply line connected to said main chamber for supplying a washing fluid to said main chamber, and a washing spit for washing said first and second pipets.

12. An apparatus as set forth in claim 11, further comprising a waste liquid line connected to said washing spit for collecting a waste washing liquid from said first and second pipets.

13. An apparatus as set forth in claim 11, further comprising a first waste liquid line connected to said washing spit for collecting a first waste washing liquid from said first and second pipets, and a second waste liquid line connected to said subchamber for collecting a second waste washing liquid from said subchamber.

* * * * *